(12) United States Patent
Ishioka

(10) Patent No.: US 8,978,478 B2
(45) Date of Patent: Mar. 17, 2015

(54) LASER ULTRASONIC FLAW DETECTION APPARATUS

(75) Inventor: Masahito Ishioka, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 276 days.

(21) Appl. No.: 13/518,926

(22) PCT Filed: Feb. 24, 2011

(86) PCT No.: PCT/JP2011/054163
§ 371 (c)(1),
(2), (4) Date: Aug. 15, 2012

(87) PCT Pub. No.: WO2011/105499
PCT Pub. Date: Sep. 1, 2011

(65) Prior Publication Data
US 2012/0304774 A1    Dec. 6, 2012

(30) Foreign Application Priority Data
Feb. 26, 2010 (JP) ................ 2010-043520

(51) Int. Cl.
*G01N 29/04* (2006.01)
*G01N 21/41* (2006.01)
*G01N 29/24* (2006.01)

(52) U.S. Cl.
CPC .... *G01N 29/2418* (2013.01); *G01N 2291/0231* (2013.01); *G01N 2291/044* (2013.01)
USPC ............... 73/643; 73/657; 73/632; 73/602

(58) Field of Classification Search
CPC .......... G01N 29/2412; G01N 29/2418; G01N 29/07; G01N 29/11; G01N 29/30; G01N 29/28; G01N 2291/0422; G01N 2291/0423; G01N 2291/02854; G01N 2291/0421; G01N 2291/044; G01N 2291/048; G01N 2291/102; G01N 2291/0427

USPC .......... 73/643, 596–600, 602, 632, 653, 657; 356/381–382, 355–357, 345; 250/231.1
See application file for complete search history.

(56) References Cited

U.S. PATENT DOCUMENTS 5,585,921 A * 12/1996 Pepper et al. .................. 356/487
5,724,138 A * 3/1998 Reich et al. .................... 356/492
(Continued)

FOREIGN PATENT DOCUMENTS

JP    7-27746      1/1995
JP    2003-508771  3/2003
(Continued)

OTHER PUBLICATIONS

International Search Report issued May 24, 2011 in corresponding International Application No. PCT/JP2011/054163 (with partial English translation).
(Continued)

*Primary Examiner* — Helen Kwok
(74) *Attorney, Agent, or Firm* — Wenderoth, Lind & Ponack, LLP

(57) ABSTRACT

A laser beam having a single wavelength emitted from a laser light source is converted at a wavelength shifter into a laser beam having at least two wavelengths, which is further demultiplexed at a beam splitter into a laser beam having a first wavelength and a laser beam having a second wavelength. The output power and pulse width of the laser beam having the first wavelength are adjusted by a first controller so as to reach levels appropriate for generating ultrasonic vibrations without causing damage to an inspection object. The output power and pulse width of the laser beam having the second wavelength are adjusted by a second controller so as to reach appropriate levels for detecting the above-described ultrasonic vibrations. These laser beams are multiplexed by a multiplexer into a single laser beam to be focused onto a surface of the inspection object.

6 Claims, 4 Drawing Sheets

(56) References Cited

U.S. PATENT DOCUMENTS

| | | | |
|---|---|---|---|
| 5,781,304 A * | 7/1998 | Kotidis et al. | 359/511 |
| 6,092,419 A * | 7/2000 | Dixon et al. | 73/602 |
| 6,335,943 B1 | 1/2002 | Lorraine et al. | |
| 7,459,337 B2 * | 12/2008 | Kang et al. | 438/99 |
| 2004/0154402 A1 * | 8/2004 | Drake, Jr. | 73/621 |
| 2006/0215175 A1 * | 9/2006 | Yacoubian | 356/502 |
| 2007/0157730 A1 * | 7/2007 | Ochiai et al. | 73/627 |
| 2007/0206203 A1 * | 9/2007 | Trainer | 356/521 |
| 2008/0007717 A1 * | 1/2008 | Nielsen et al. | 356/73 |
| 2008/0016965 A1 | 1/2008 | Drake et al. | |
| 2008/0291963 A1 | 11/2008 | Deaton, Jr. et al. | |
| 2009/0122322 A1 * | 5/2009 | Pouet | 356/497 |
| 2009/0272191 A1 * | 11/2009 | Maris et al. | 73/618 |
| 2012/0067128 A1 * | 3/2012 | Oberhoff et al. | 73/632 |

FOREIGN PATENT DOCUMENTS

| | | |
|---|---|---|
| JP | 2006-125996 | 5/2006 |
| JP | 2009-544038 | 12/2009 |

OTHER PUBLICATIONS

Written Opinion of the International Searching Authority issued May 24, 2011 in corresponding International Application No. PCT/JP2011/054163 (with English translation).

Decision to Grant a Patent issued Mar. 19, 2013 in corresponding Japanese Application No. 2010-043520.

* cited by examiner

LASER ULTRASONIC FLAW DETECTION APPARATUS

TECHNICAL FIELD

The present invention relates to a laser ultrasonic flaw detection apparatus that is employed to perform non-destructive flaw detection of a defect or the like inside an inspection object.

BACKGROUND ART

In recent years, the use of composite materials is increasing in aerospace, automobile and other industries for the purpose of reducing product weight, etc. A laser ultrasonic flaw detection apparatus is employed as a method of non-destructively evaluating the structural integrity of such composite materials, etc.

The principle of this laser ultrasonic flaw detection apparatus will be briefly described. First, when a first laser beam is focused onto a surface of an inspection object, ultrasonic vibrations are generated due to the thermoelastic effect. Specifically, the surface of the inspection object is heated by the laser beam; the volume of the inspection object expands along with this increase in temperature, thus generating stress; and ultrasonic vibrations are generated by this stress.

The ultrasonic vibrations propagate from the surface of the inspection object to the interior thereof, and, if there is a defect inside the inspection object, the ultrasonic vibrations are reflected at this defect site thus vibrating the surface of the inspection object again. When a second laser beam is focused onto this vibrating surface of the inspection object, the second laser beam is reflected at the surface of the inspection object, and the ultrasonic vibrations reflected at the defect site inside the inspection object are superimposed on the reflected light. Therefore, flaw detection can be performed for a defect inside an inspection object by extracting the ultrasonic vibrations by guiding the reflected light of the second laser beam to a laser interferometer or the like. At this time, in order to guide only the second laser beam to the laser interferometer without guiding the first laser beam to the laser interferometer, the wavelength of the first laser beam is made different from the wavelength of the second laser beam, and only the reflected light of the first laser beam is removed with a wavelength filter (see Patent Literatures 1 to 3).

CITATION LIST

Patent Literature

{PTL 1} U.S. Patent Application, Publication No. 2008/0291963, Specification
{PTL 2} U.S. Patent Application, Publication No. 2008/0016965, Specification
{PTL 3} Japanese Translation of PCT International Application, Publication No. 2003-508771

SUMMARY OF INVENTION

Technical Problem

However, such a laser ultrasonic flaw detection apparatus has the following problems.

In order to generate appropriate ultrasonic vibrations in an inspection object without causing damage, such as ablation, etc., it is necessary to adjust the output power and pulse width of the first laser beam to appropriate levels in accordance with the material, size, etc. of the inspection object. In addition, in order to prevent the second laser beam from affecting the ultrasonic vibrations generated in the inspection object by the first laser beam, it is also necessary to adjust the output power and pulse width of the second laser beam to appropriate levels. This control of the output powers and the pulse widths of the first laser beam and the second laser beam has been performed by directly adjusting the laser light sources that emit the first laser beam and the second laser beam. Because of this, control ranges for the output powers and the pulse widths of the laser beams are restricted to narrow ranges, and there are cases in which sufficient adjustment cannot be performed for the output powers and the pulse widths of the laser beams to achieve appropriate levels in accordance with the type of inspection object.

In addition, in order to guide only the reflected light of the second laser beam for detecting the ultrasonic vibrations to the laser interferometer without guiding the reflected light of the first laser beam for generating the ultrasonic vibrations to the laser interferometer, as described above, the wavelength of the first laser beam is made different from the wavelength of the second laser beam, and only the reflected light of the first laser beam is removed with the wavelength filter. Two types of laser light sources are required to generate the first laser beam and the second laser beam, and this fact has caused an increase in size of laser ultrasonic flaw detection apparatuses.

Furthermore, the laser beams in the laser ultrasonic flaw detection apparatus are guided by bulk optical elements, such as lenses, mirrors, and so on. Therefore, with regard to individual constituent elements through which the laser beams pass in the laser ultrasonic flaw detection apparatus, securing fixtures are required to ensure sufficient alignment precision, and the degree of freedom in placing these individual constituent elements in the laser ultrasonic flaw detection apparatus is limited. As a result, the size of the laser ultrasonic flaw detection apparatus is increased, thus resulting in poor portability thereof. Because of this, when performing flaw-detection inspection in individual parts of the inspection object, it is necessary to move the inspection object so that the laser ultrasonic flaw detection apparatus is placed against these individual parts, and it is thus particularly difficult to perform flaw detection inspection for an inspection object whose weight and size are large.

The present invention has been conceived in light of the above-described circumstances, and an object thereof is to provide a laser ultrasonic flaw detection apparatus that, by simplifying the apparatus configuration, is made compact, lightweight, and easy to handle, and that also has wide control ranges for the output powers and pulse widths of the laser beams.

Solution to Problem

In order to solve the above-described problems, the present invention employs the following solutions.

A laser ultrasonic flaw detection apparatus according to the present invention is a laser ultrasonic flaw detection apparatus in which a first laser beam is focused onto a surface of an inspection object; a second laser beam is focused onto the surface of the inspection object to detect reflected waves reflected at the surface of the inspection object, thereby acquiring a vibration displacement at the surface of the inspection object excited by ultrasonic waves generated by the first laser beam; and the presence/absence of a defect inside the inspection object, which is reflected in the vibration displacement, is detected, the laser ultrasonic flaw detection apparatus including a laser light source that emits a laser beam having a single wavelength; a wavelength shifter that converts the laser beam emitted from the laser light source into a laser beam that includes at least two wavelengths; a beam splitter that demultiplexes the laser beam converted by the wavelength shifter into a laser beam having a first wavelength and a laser beam having a second wavelength which is different from the first wavelength; a first controller that adjusts the output power and pulse width of the laser beam having the first wavelength passed through the beam splitter; a second controller that adjusts the output power and pulse width of the laser beam having the second wavelength passed through the beam splitter; a multiplexer that multiplexes the laser beam having the first wavelength, which has been adjusted by the first controller, and the laser beam having the second wavelength, which has been adjusted by the second controller, and that passes a single laser beam including the laser beam having the first wavelength and the laser beam having the second wavelength; and an optical projection unit that projects the single laser beam obtained at the multiplexer to the surface of the inspection object, wherein the laser beam having the first wavelength is used as the first laser beam and the laser beam having the second wavelength is used as the second laser beam.

With this laser ultrasonic flaw detection apparatus, because the first laser beam for generating the ultrasonic waves in the inspection object and the second laser beam for detecting the ultrasonic vibrations generated in the inspection object are emitted from the same laser light source, as compared with the case in which a laser light source that emits the first laser beam and a laser light source that emits the second laser beam are separately prepared, the configuration of the laser ultrasonic flaw detection apparatus can be simplified.

Here, although the single laser beam, which includes both the first laser beam and the second laser beam, is focused onto the surface of the inspection object, in order to acquire the ultrasonic vibrations generated in the inspection object, it is necessary to detect only the second laser beam without detecting the first laser beam. Therefore, the single laser beam, which includes the first laser beam and the second laser beam, is focused onto the surface of the inspection object; the reflected waves reflected at the surface of the inspection object are made to pass through the wavelength filter, which blocks the beam having the first wavelength but transmits the beam having the second wavelength, thereby removing only the first laser beam; and it is possible to detect only the second laser beam that has passed through the wavelength filter.

Furthermore, the laser ultrasonic flaw detection apparatus is provided with the first controller that adjusts the output power and the pulse width of the laser beam having the first wavelength, that is, the first laser beam, and the second controller that adjusts the output power and the pulse width of the laser beam having the second wavelength, that is, the second laser beam. Therefore, as compared with the case in which the output power and pulse width of a laser beam are adjusted in a laser light source, control ranges for the output power and pulse width of the laser beam can be considerably increased. In addition, the adjustment of the output power/pulse width for the first laser beam and the adjustment of the output power/pulse width for the second laser beam can be performed independently of each other. Accordingly, it is possible to easily set the output power/pulse width of the first laser beam to levels for generating appropriate ultrasonic vibrations without causing damage to the inspection object, while also setting the output power/pulse width of the second laser beam to appropriate levels for detecting the ultrasonic vibrations generated in the inspection object, in accordance with the type and size of the inspection object.

In the laser ultrasonic flaw detection apparatus of the present invention, it is preferable that the laser beam transmitted between at least two of the laser light source, the wavelength shifter, the beam splitter, the first controller, the second controller, the multiplexer, and the optical projection unit be guided by an optical fiber.

With this configuration, as compared with the case in which the laser beams are guided by bulk optical elements, such as lenses and mirrors, to be transmitted among the individual constituent elements of the laser ultrasonic flaw detection apparatus, such as the laser light source, the wavelength shifter, the beam splitter, the first controller, the second controller, the multiplexer, optical projection unit, etc., the degree of freedom for the placement of the individual constituent elements in the laser ultrasonic flaw detection apparatus is increased, and, also, there is no need for securing fixtures for ensuring the alignment precision of the individual constituent elements. Therefore, the structure of the laser ultrasonic flaw detection apparatus can be simplified, and the laser ultrasonic flaw detection apparatus can be made compact.

In addition, in the laser ultrasonic flaw detection apparatus of this invention, it is preferable that the laser light source, the wavelength shifter, the beam splitter, the first controller, the second controller, and the multiplexer be accommodated in a laser-ultrasonic-flaw-detection-apparatus main unit; the optical projection unit be accommodated in a flaw detection head that can be moved with respect to the laser-ultrasonic-flaw-detection-apparatus main unit; and the laser beam that is transmitted between the laser-ultrasonic-flaw-detection-apparatus main unit and the flaw detection head be guided by an optical fiber.

With this configuration, the flaw detection head, in which the optical projection unit that guides the laser beams to the surface of the inspection object is accommodated, can be moved with respect to the laser-ultrasonic-flaw-detection-apparatus main unit, which accommodates other constituent elements of the laser ultrasonic flaw detection apparatus. Here, because only the optical projection unit is accommodated in the flaw detection head, the weight/size of the flaw detection head is very small as compared with the weight/size of the laser ultrasonic flaw detection apparatus as a whole. Therefore, by moving the flaw detection head with respect to the main unit of the laser ultrasonic flaw detection apparatus, an irradiation position of the laser beam can be easily changed/adjusted to a desired position.

Specifically, when changing/adjusting the irradiation position of the laser beam, it is not necessary to move the inspection object with respect to the laser ultrasonic flaw detection apparatus, and it suffices to move only the flaw detection head of the laser ultrasonic flaw detection apparatus to an inspection target site of the inspection object while keeping the inspection object stationary. In particular, even in the case in which the weight and size of the inspection object are large, flaw detection inspection can be performed for the individual parts of the inspection object by focusing the laser beam onto desired sites of the inspection object without moving the inspection object.

In addition, in the laser ultrasonic flaw detection apparatus of the present invention, it is preferable that the wavelength shifter be provided with a nonlinearity-inducing fiber.

Alternatively, in the laser ultrasonic flaw detection apparatus, it is preferable that the wavelength shifter be provided with a sideband spectrum optical modulator.

In addition, it is preferable that the laser ultrasonic flaw detection apparatus of the present invention be additionally provided with a photo detector unit that receives reflected waves of the single laser beam that is projected onto the surface of the inspection object by the optical projection unit and is reflected at the surface of the inspection object; a wavelength filter that, of the single laser beam received by the photo detector unit, blocks the laser beam having the first wavelength and transmits the laser beam having the second wavelength; and a laser interferometer that detects the laser beam having the second wavelength that has passed through the wavelength filter.

Advantageous Effects of Invention

With a laser ultrasonic flaw detection apparatus of the present invention, because the apparatus configuration is simplified and the apparatus size is reduced, when changing/adjusting an irradiation position of a laser beam on an inspection object, the apparatus can be easily handled. Moreover, with the laser ultrasonic flaw detection apparatus of the present invention, because the control ranges for the output power and pulse width of the laser beam are large, the output power and pulse width of the laser beam can be set to optimal levels in accordance with the type and size of the inspection object.

DESCRIPTION OF EMBODIMENT

An embodiment of a laser ultrasonic flaw detection apparatus according to the present invention will be described below with reference to the drawings.

A laser ultrasonic flaw detection apparatus according to this embodiment focuses a first laser beam onto a surface of an inspection object. In addition, the laser ultrasonic flaw detection apparatus focuses a second laser beam, which is different from the first laser beam, onto the surface of the inspection object. Accordingly, a vibration displacement at the surface of the inspection object excited by ultrasonic waves generated by the first laser beam is superimposed on reflected waves of the second laser beam reflected at the surface of the inspection object. By detecting the reflected waves of the second laser beam, the laser ultrasonic flaw detection apparatus acquires the vibration displacement excited at the surface of the inspection object due to the ultrasonic waves generated by the first laser beam, and detects the presence/absence of a defect inside the inspection object, which is reflected in this vibration displacement.

Figure 1:
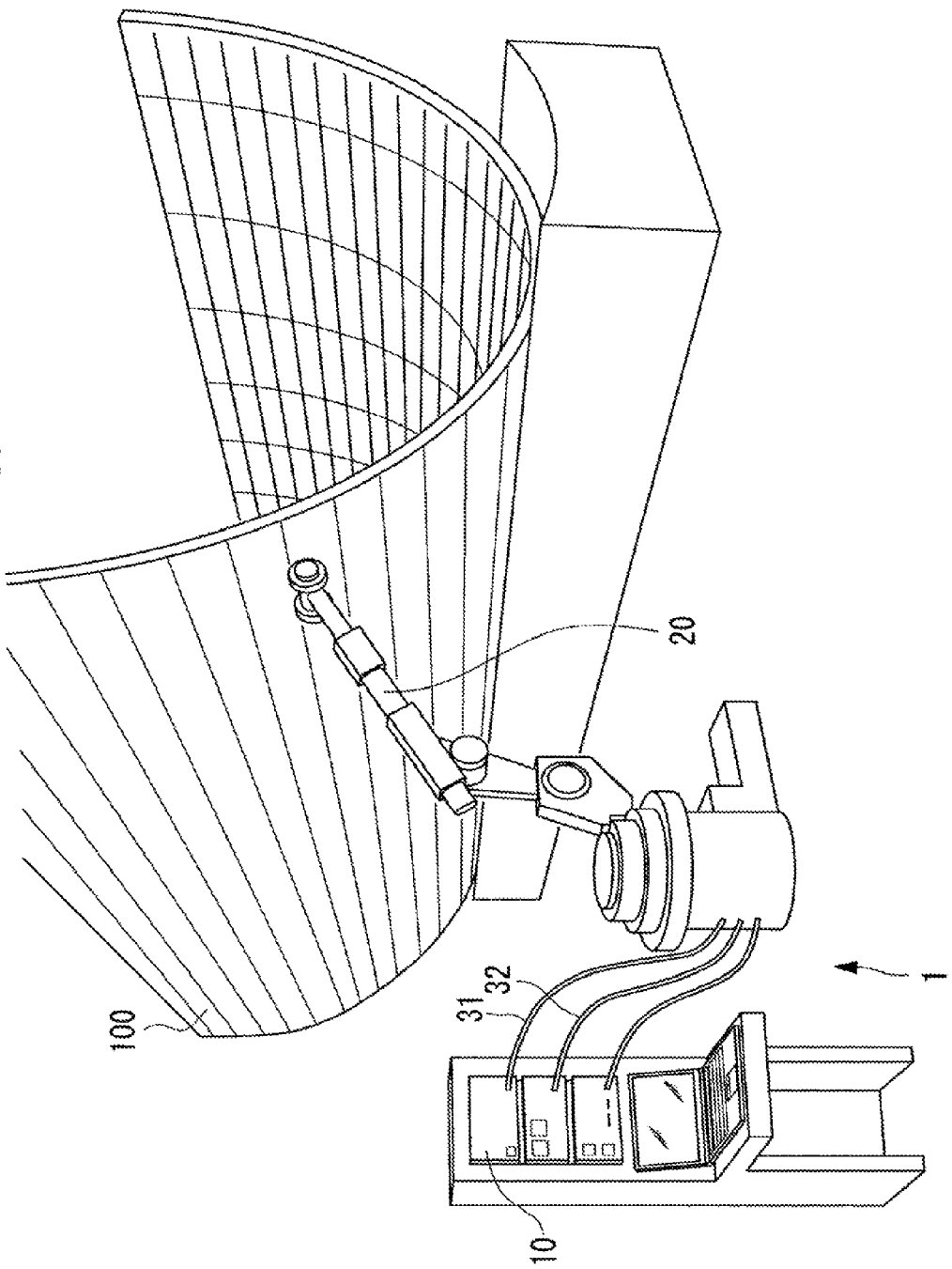
FIG. 1 is a perspective view showing the overall configuration of a laser ultrasonic flaw detection apparatus according to the present invention and a usage example thereof.

FIG. 1 shows the overall configuration of the laser ultrasonic flaw detection apparatus according to this embodiment and the usage thereof.

As shown in FIG. 1, a laser ultrasonic flaw detection apparatus 1 is configured including a laser-ultrasonic-flaw-detection-apparatus main unit 10, a flaw detection head 20 that can be moved with respect to the laser-ultrasonic-flaw-detection-apparatus main unit 10, optical fibers 31 and 32 that connect the laser-ultrasonic-flaw-detection-apparatus main unit 10 and the flaw detection head 20 so as to guide laser beams between the laser-ultrasonic-flaw-detection-apparatus main unit 10 and the flaw detection head 20.

Figure 2:
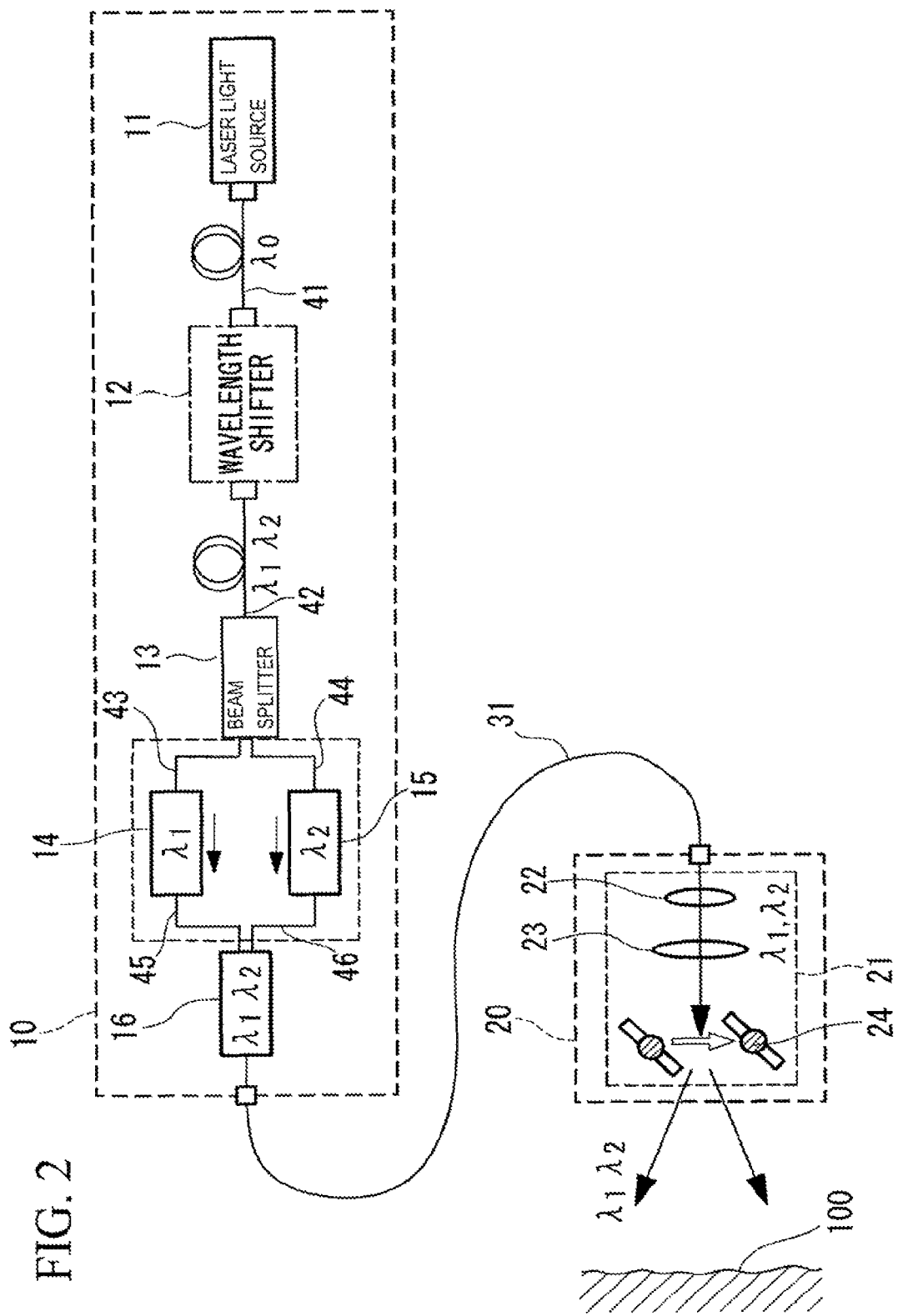
FIG. 2 is a schematic diagram showing a laser-beam optical projection system of the laser ultrasonic flaw detection apparatus according to the present invention.
Figure 3:
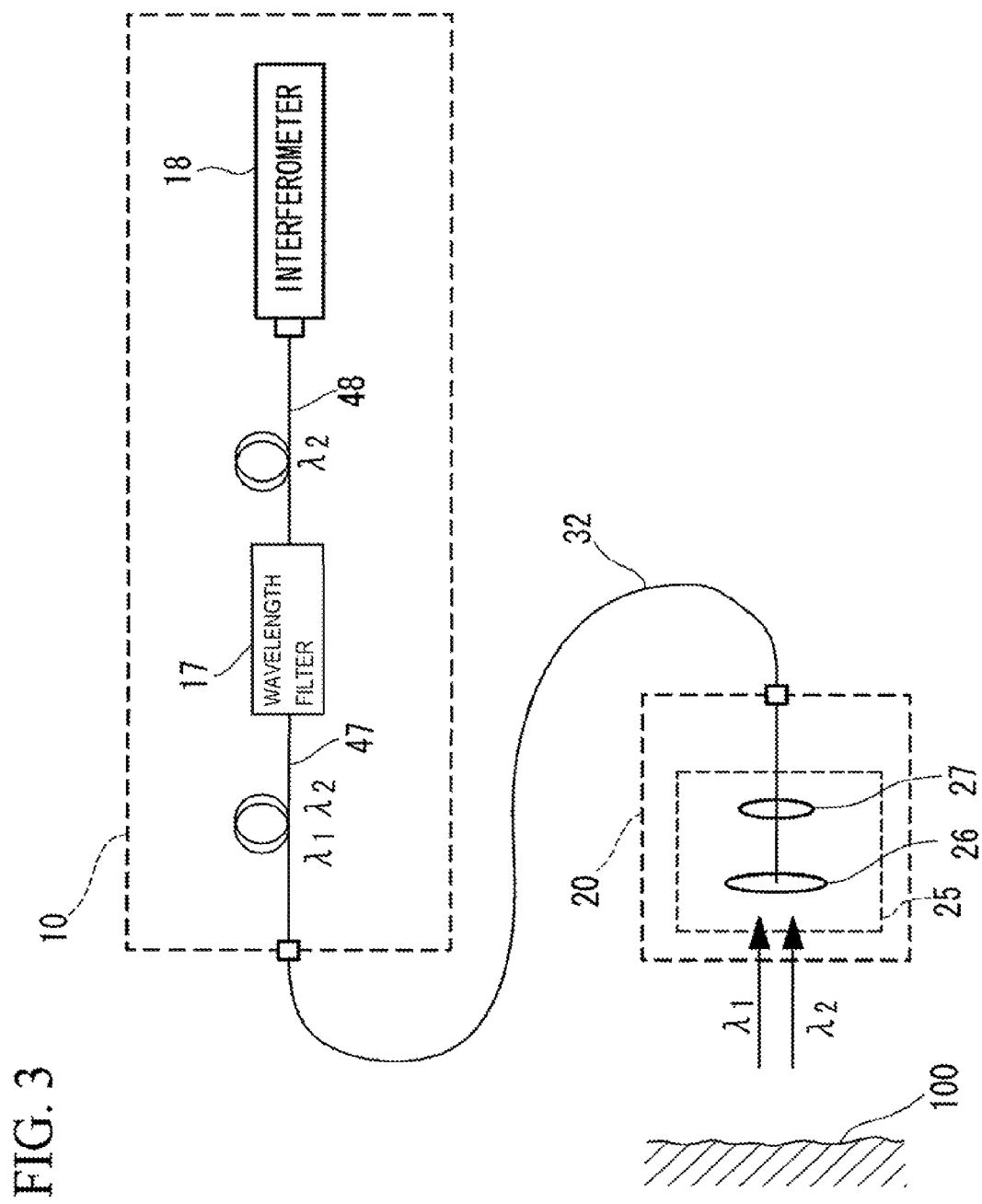
FIG. 3 is a schematic diagram showing a laser-beam photo detector system of the laser ultrasonic flaw detection apparatus according to the present invention.

The internal configuration of the laser ultrasonic flaw detection apparatus 1 is shown in FIGS. 2 and 3.

The laser ultrasonic flaw detection apparatus 1 is roughly divided into a laser-beam optical projection system (see FIG. 2) that emits the first laser beam and the second laser beam, with which an inspection object 100 is irradiated, and a laser-beam photo detector system (see FIG. 3) that receives and detects reflected waves from the surface of the inspection object 100.

As shown in FIGS. 2 and 3, the laser-ultrasonic-flaw-detection-apparatus main unit 10 is configured including a laser light source 11, a wavelength shifter 12, a beam splitter 13, a first controller 14, a second controller 15, a multiplexer 16, a wavelength filter 17, a laser interferometer 18, and optical fibers 41 to 48.

In addition, as shown in FIGS. 2 and 3, the flaw detection head 20 is configured including an optical projection unit 21 and a photo detector unit 25.

The laser light source 11 emits a laser beam having a single wavelength $\lambda_0$. The laser beam emitted from the laser light source 11 is guided to the wavelength shifter 12 through the optical fiber 41. The wavelength shifter 12 converts the laser beam having the single wavelength $\lambda_0$ emitted from the laser light source 11 into a laser beam that includes two wavelengths $\lambda_1$ and $\lambda_2$.

The method of converting the wavelength of the laser beam at the wavelength shifter 12 will be described with reference to FIGS. 4 and 5.

Figure 4:
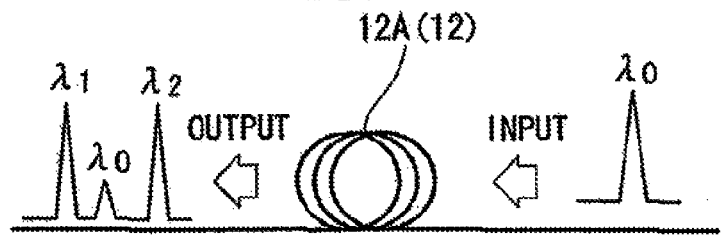
FIG. 4 is a schematic diagram showing a method of converting the wavelength of a laser beam at a wavelength shifter.

In an example shown in FIG. 4, the wavelength shifter 12 has a nonlinearity-inducing fiber 12A.

Upon receiving the input laser beam having the single wavelength $\lambda_0$, the nonlinearity-inducing fiber 12A outputs the laser beams including the two wavelengths $\lambda_1$ and $\lambda_2$ via the Raman effect or the Brillouin effect. Here, one of $\lambda_1$ and $\lambda_2$ may be equal to $\lambda_0$.

Figure 5:
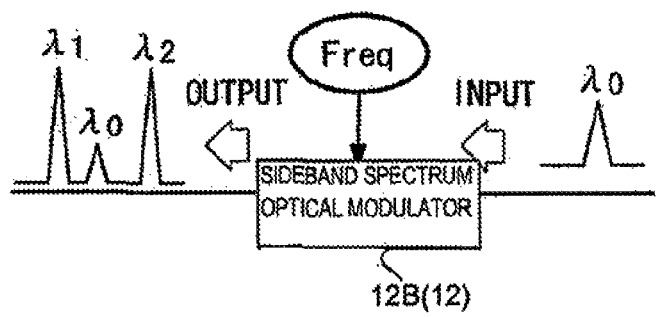
FIG. 5 is a schematic diagram showing another example of the method of converting the wavelength of the laser beam at the wavelength shifter.

In an example shown in FIG. 5, the wavelength shifter 12 has a sideband spectrum optical modulator 12B. Upon receiving the input laser beam having the single wavelength $\lambda_0$, the sideband spectrum optical modulator 12B outputs the laser beam including the wavelength $\lambda_1$, which is shorter than $\lambda_0$, and the wavelength $\lambda_2$, which is longer than $\lambda_0$.

As shown in FIG. 2, the laser beam including two wavelengths $\lambda_1$ and $\lambda_2$, which is obtained by converting the wavelength of the laser beam having the single wavelength $\lambda_0$ with the wavelength shifter 12, is guided to the beam splitter 13 through the optical fiber 42. The beam splitter 13 demultiplexes the laser beam including the two wavelengths $\lambda_1$ and $\lambda_2$ into a laser beam including the first wavelength $\lambda_1$ and a laser beam having the second wavelength $\lambda_2$ and passes them.

The laser beam having the first wavelength $\lambda_1$, which has been demultiplexed at and passed through the beam splitter 13, is guided to the first controller 14 through the optical fiber 43. The first controller 14 adjusts the output power and a pulse width of this laser beam having the first wavelength $\lambda_1$. Similarly, the laser beam having the second wavelength $\lambda_2$, which has been demultiplexed at and passed through the beam splitter 13, is guided to the second controller 15 through the optical fiber 44. The second controller 15 adjusts the output power and a pulse width of this laser beam having the second wavelength $\lambda_2$.

Figure 6:
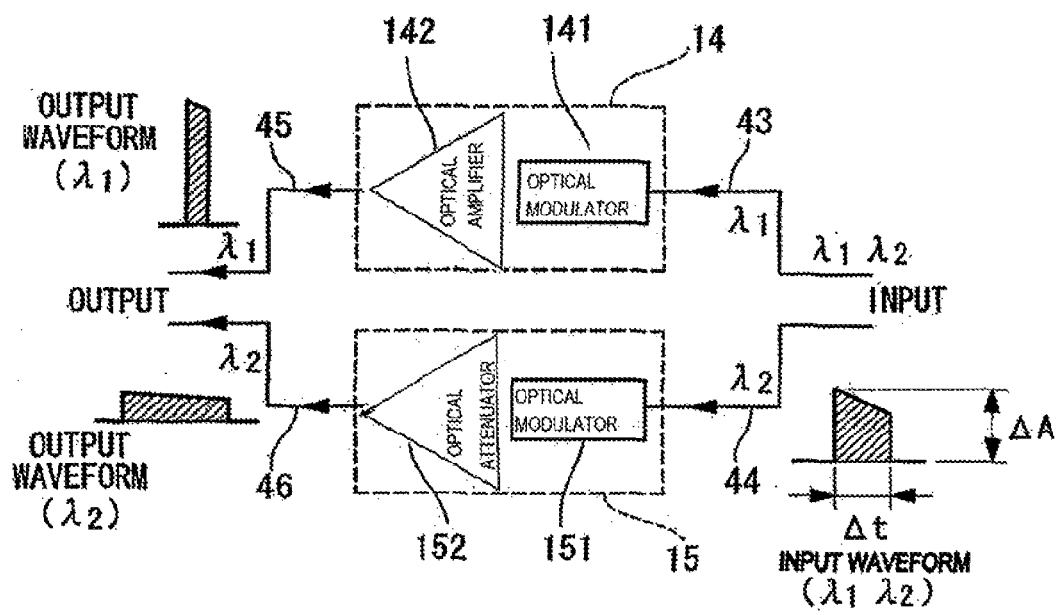
FIG. 6 is a schematic diagram showing the configurations of a first controller and a second controller.

FIG. 6 shows the adjustment status of the output powers and the pulse widths of the laser beam having the first wavelength $\lambda_1$ and the laser beam having the second wavelength $\lambda_2$ at the first controller 14 and the second controller 15.

The first controller 14 has an optical modulator 141 and an optical amplifier 142. The optical modulator 141 adjusts (mainly reduces) the pulse width of the laser beam having the first wavelength $\lambda_1$. Then, the output power of the laser beam having the first wavelength $\lambda_1$ is increased by the optical amplifier 142.

By doing so, the first controller 14 adjusts the output power and the pulse width of the laser beam having the first wavelength $\lambda_1$ in accordance with the material and size of the inspection object 100. Specifically, the output power of the laser beam having the first wavelength $\lambda_1$ is set to a level such that the laser beam is easily absorbed to a desired depth in the inspection object 100 to cause thermoelastic expansion without causing damage, such as ablation, etc., to the inspection object 100 with the laser beam having the first wavelength $\lambda_1$. The pulse width of the laser beam having the first wavelength $\lambda_1$ is set to a sufficient level to induce ultrasonic vibrations in the inspection object 100.

The second controller 15 has an optical modulator 151 and an optical attenuator 152. The optical modulator 151 is a chirp element that increases the pulse width of the laser beam having the second wavelength $\lambda_2$. Then, the output power of the laser beam having the second wavelength $\lambda_2$ is decreased by the optical attenuator 152.

In this way, the second controller 15 adjusts the output power and the pulse width of the laser beam having the second wavelength $\lambda_2$ so that it has an output power and a pulse width appropriate for detecting the ultrasonic vibrations generated in the inspection object 100 by the laser beam having the first wavelength $\lambda_1$. The output power and the pulse width of the laser beam having the second wavelength $\lambda_2$ are adjusted to levels that do not induce ultrasonic vibrations in the inspection object 100.

As shown in FIG. 2, the laser beam having the first wavelength $\lambda_1$, whose output power and pulse width have been adjusted by the first controller 14, is guided to the multiplexer 16 through the optical fiber 45. Similarly, the laser beam having the second wavelength $\lambda_2$, whose output power and pulse width have been adjusted by the second controller 15, is guided to the multiplexer 16 through the optical fiber 46. Then, the multiplexer 16 multiplexes the laser beam having the first wavelength $\lambda_1$, which has been adjusted by the first controller 14, and the laser beam having the second wavelength $\lambda_2$, which has been adjusted by the second controller 15, and passes a single laser beam that includes the laser beam having the first wavelength $\lambda_1$ and the laser beam having the second wavelength $\lambda_2$.

This single laser beam is output from the main unit of the laser ultrasonic flaw detection apparatus 10 and is guided to the optical projection unit 21 of the flaw detection head 20 through the optical fiber 31.

The optical projection unit 21 has lenses 22 and 23 and a scanning mirror 24. With these lenses 22 and 23 and the scanning mirror 24, the single laser beam including the laser beam having the first wavelength $\lambda_1$ and the laser beam having the second wavelength $\lambda_2$ is guided to the surface of the inspection object 100.

Of the single laser beam including the laser beam having the first wavelength $\lambda_1$ and the laser beam having the second wavelength $\lambda_2$ focused onto the surface of the inspection object 100, the thermoelastic expansion caused by the first laser beam when absorbed by the inspection object 100 generates ultrasonic vibrations in the inspection object 100. The ultrasonic vibrations generated in the inspection object 100 propagate in the inspection object 100. Then, if there is a defect at an interface of or inside the inspection object 100, the ultrasonic vibrations are reflected there and return to the surface of the inspection object 100, and the reflected ultrasonic waves cause vibrations at the surface of the inspection object 100. As described above, the laser bean having the second wavelength $\lambda_2$ is not involved in the generation of ultrasonic vibrations in the inspection object 100.

The single laser beam including the laser beam having the first wavelength $\lambda_1$ and the laser beam having the second wavelength $\lambda_2$ returns to the flaw detection head 20 again, after being reflected at the surface of the inspection object 100.

Here, of the single laser beam, when the laser beam having the second wavelength $\lambda_2$, which is not involved in the generation of the ultrasonic vibrations in the inspection object 100, is reflected at the surface of the inspection object 100, the ultrasonic vibrations are generated in the inspection object 100. Therefore, the supersonic vibrations that have been reflected at the defect in the inspection object 100 and returned to the surface of the inspection object 100 are superimposed on the reflected waves of the laser beam having the second wavelength $\lambda_2$. As a result, by detecting the reflected waves of the laser beam having the second wavelength $\lambda_2$, the inspection object 100 can be inspected for the presence/absence of a flaw.

As shown in FIG. 3, the single laser beam, reflected at the surface of the inspection object 100, which includes the laser beam having the first wavelength $\lambda_1$ and the laser beam having the second wavelength $\lambda_2$, is collected by a photo detector lens 26 and a fiber focusing lens 27 of the photo detector unit 25 accommodated in the flaw detection head 20, and is sent to the laser-ultrasonic-flaw-detection-apparatus main unit 10 through the optical fiber 32.

The laser beam sent to the laser-ultrasonic-flaw-detection-apparatus main unit 10 is input to the wavelength filter 17 through the optical fiber 47. The wavelength filter 17 is configured to block the beam having the first wavelength $\lambda_1$ but to transmit the beam having the second wavelength $\lambda_2$. Therefore, of the single laser beam reflected at the surface of the inspection object 100, only the laser beam having the second wavelength $\lambda_2$ is output from the wavelength filter 17. Then, the laser beam having the second wavelength $\lambda_2$ is input to the laser interferometer 18. As described above, because the ultrasonic vibrations that have returned to the surface of the inspection object 100 by being reflected at the defect in the inspection object 100 are superimposed on reflected waves of the laser beam having the second wavelength $\lambda_2$, by extracting the ultrasonic vibrations in the laser beam having the second wavelength $\lambda_2$ which is input to the laser interferometer 18, the presence/absence of a defect in the inspection object 100 can be detected.

With this laser ultrasonic flaw detection apparatus 1, because the first laser beam for generating the ultrasonic waves in the inspection object 100 and the second laser beam for detecting the ultrasonic vibrations generated in the inspection object are emitted by the same laser light source 11, as compared with the case in which a laser light source that emits the first laser beam and a laser light source that emits the second laser beam are separately prepared, the configuration of the laser ultrasonic flaw detection apparatus can be simplified.

Here, the single laser beam, which includes both the first laser beam and the second laser beam, is focused onto the surface of the inspection object.

In order to acquire the ultrasonic vibrations generated in the inspection object 100, it is necessary to detect only the second laser beam without detecting the first laser beam. Therefore, the single laser beam, which includes the first laser beam and the second laser beam, is focused onto the surface of the inspection object; the reflected waves reflected at the surface of the inspection object are made to pass through the wavelength filter 17, which blocks the beam having the first wavelength $\lambda_1$ but transmits a beam having the second wavelength $\lambda_2$, thereby removing only the first laser beam; and only the second laser beam that has passed through the wavelength filter 17 can be detected by the laser interferometer 18.

Furthermore, the laser ultrasonic flaw detection apparatus 1 is provided with the first controller 14 that adjusts the output power and the pulse width of the laser beam having the first wavelength $\lambda_1$, that is, the first laser beam, and the second controller 15 that adjusts the output power and the pulse width of the laser beam having the second wavelength $\lambda_2$, that is, the second laser beam. Therefore, as compared with the case in which the output power and pulse width of a laser beam are adjusted in a laser light source, control ranges for the output power and pulse width of the laser beam can be considerably increased. In addition, the adjustment of the output power/pulse width for the first laser beam and the adjustment of the output power/pulse width for the second laser beam can be performed independently of each other. Accordingly, it is possible to easily set the output power/pulse width of the first laser beam to levels for generating appropriate ultrasonic vibrations without causing damage to the inspection object, while also setting the output power/pulse width of the second laser beam to appropriate levels for detecting the ultrasonic vibrations generated in the inspection object, in accordance with the type and size of the inspection object 100.

In addition, as compared with the case in which the laser beams are guided by bulk optical elements, such as lenses and mirrors, to be transmitted among the individual constituent elements of the laser ultrasonic flaw detection apparatus 1, such as the laser light source 11, the wavelength shifter 12, the beam splitter 13, the first controller 14, the second controller 15, the multiplexer 16, the optical projection unit 21, the photo detector unit 25, etc., the degree of freedom for the placement of the individual constituent elements in the laser ultrasonic flaw detection apparatus 1 is increased, and, also, there is no need for securing fixtures for ensuring the alignment precision of the individual constituent elements. Therefore, the structure of the laser ultrasonic flaw detection apparatus 1 can be simplified, and the laser ultrasonic flaw detection apparatus 1 can be made compact.

In addition, the flaw detection head 20, in which an optical projection unit 21 that guides the laser beams to the surface of the inspection object 100 is accommodated, can be moved with respect to the laser-ultrasonic-flaw-detection-apparatus main unit 10, which accommodates other constituent elements 11 to 16 of the laser ultrasonic flaw detection apparatus 1. Here, because only the optical projection unit 21 and the photo detector unit 25 are accommodated in the flaw detection head, the weight/size of the flaw detection head 20 is very small as compared with the weight/size of the laser ultrasonic flaw detection apparatus 1 as a whole. Therefore, by moving the flaw detection head 20 with respect to the laser-ultrasonic-flaw-detection-apparatus main unit 10, an irradiation position of the laser beam can be easily changed/adjusted to a desired position.

Specifically, when changing/adjusting the irradiation position of the laser beam, it is not necessary to move the inspection object 100 with respect to the laser ultrasonic flaw detection apparatus 1, and it suffices to move only the flaw detection head 20 of the laser ultrasonic flaw detection apparatus 1 to an inspection target site of the inspection object 100 while keeping the inspection object 100 stationary. In particular, even in the case in which the weight and size of the inspection object 100 are large, flaw detection inspection can be performed for the individual parts of the inspection object 100 by focusing the laser beam onto desired sites of the inspection object 100 without moving the inspection object 100.

Although the embodiment of the present invention has been described above in detail with reference to the drawings, specific configurations are not limited to this embodiment, and design alterations, or the like, within a range that does not depart from the spirit of the present invention are also encompassed.

REFERENCE SIGNS LIST

1 laser ultrasonic flaw detection apparatus
10 laser-ultrasonic-flaw-detection-apparatus main unit
11 laser light source
12 wavelength shifter
12A nonlinearity-inducing fiber
12B sideband spectrum optical modulator
13 beam splitter
14 first controller
15 second controller
16 multiplexer
17 wavelength filter
18 laser interferometer
20 flaw detection head
21 optical projection unit
25 photo detector unit
31, 32, 41 to 48 optical fiber
100 inspection object

The invention claimed is:

1. A laser ultrasonic flaw detection apparatus in which:
a first laser beam is focused onto a surface of an inspection object;
a second laser beam is focused onto the surface of the inspection object to detect reflected waves reflected at the surface of the inspection object, thereby acquiring a vibration displacement at the surface of the inspection object excited by ultrasonic waves generated by the first laser beam; and the presence/absence of a defect inside the inspection object, which is reflected in the vibration displacement, is detected; the laser ultrasonic flaw detection apparatus comprising:
a laser light source that emits a laser beam having a single wavelength;
a wavelength shifter that converts the laser beam emitted from the laser light source into a laser beam that includes at least two wavelengths;
a beam splitter that demultiplexes the laser beam converted by the wavelength shifter into a laser beam having a first wavelength and a laser beam having a second wavelength which is different from the first wavelength;
a first controller that adjusts output power and pulse width of the laser beam having the first wavelength passed through the beam splitter;

a second controller that adjusts output power and pulse width of the laser beam having the second wavelength passed through the beam splitter;

a multiplexer that multiplexes the laser beam having the first wavelength, which has been adjusted by the first controller, and the laser beam having the second wavelength, which has been adjusted by the second controller, and that passes a single laser beam including the laser beam having the first wavelength and the laser beam having the second wavelength; and an optical projection unit that projects the single laser beam obtained at the multiplexer to the surface of the inspection object, wherein the laser beam having the first wavelength is used as the first laser beam and the laser beam having the second wavelength is used as the second laser beam.

2. A laser ultrasonic flaw detection apparatus according to claim 1, wherein at least one of the laser beam having the single wavelength, transmitted between the laser light source and the wavelength shifter, the laser beam including the at least two wavelengths, transmitted between the wavelength shifter and the beam splitter, the laser beam having the first wavelength, transmitted between the beam splitter and the first controller, the laser beam having the second wavelength, transmitted between the beam splitter and the second controller, the laser beam adjusted by the first controller, transmitted between the first controller and the multiplexer, the laser beam adjusted by the second controller, transmitted between the second controller and the multiplexer, and the single laser beam transmitted between the multiplexer and the optical projection unit, is guided by an optical fiber.

3. A laser ultrasonic flaw detection apparatus according to claim 1, wherein:

the laser light source, the wavelength shifter, the beam splitter, the first controller, the second controller, and the multiplexer are accommodated in a laser-ultrasonic-flaw-detection-apparatus main unit;

the optical projection unit is accommodated in a flaw detection head that can be moved with respect to the laser-ultrasonic-flaw-detection-apparatus main unit; and the single laser beam that is transmitted between the laser-ultrasonic-flaw-detection-apparatus main unit and the flaw detection head is guided by an optical fiber.

4. A laser ultrasonic flaw detection apparatus according to claim 1, wherein the wavelength shifter has a nonlinearity-inducing fiber.

5. A laser ultrasonic flaw detection apparatus according to claim 1 wherein the wavelength shifter has a sideband spectrum optical modulator.

6. A laser ultrasonic flaw detection apparatus according to claim 1, further comprising:

a photo detector unit that receives reflected waves of the single laser beam that is projected onto the surface of the inspection object by the optical projection unit and is reflected at the surface of the inspection object;

a wavelength filter that, of the single laser beam received by the photo detector unit, blocks the laser beam having the first wavelength and transmits the laser beam having the second wavelength; and a laser interferometer that detects the laser beam having the second wavelength that has passed through the wavelength filter.

* * * * *